United States Patent
Harada et al.

(10) Patent No.: US 11,414,557 B2
(45) Date of Patent: Aug. 16, 2022

(54) ACTIVE-ENERGY-RAY-POLYMERIZABLE INITIATOR, ACTIVE-ENERGY-RAY-POLYMERIZABLE COMPOSITION, ACTIVE-ENERGY-RAY-POLYMERIZABLE INK, INK STORAGE CONTAINER, IMAGE FORMING METHOD, AND IMAGE FORMING APPARATUS

(71) Applicant: RICOH COMPANY, LTD., Tokyo (JP)

(72) Inventors: Shigeyuki Harada, Shizuoka (JP); Hidetoshi Fujii, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 390 days.

(21) Appl. No.: 16/774,636

(22) Filed: Jan. 28, 2020

(65) Prior Publication Data
US 2020/0270469 A1 Aug. 27, 2020

(30) Foreign Application Priority Data
Feb. 26, 2019 (JP) .............................. JP2019-033066

(51) Int. Cl.
| | |
|---|---|
| *C09D 11/101* | (2014.01) |
| *C07C 271/22* | (2006.01) |
| *B41J 2/175* | (2006.01) |
| *B41M 5/00* | (2006.01) |
| *C07C 69/78* | (2006.01) |
| *C09D 11/00* | (2014.01) |

(52) U.S. Cl.
CPC ......... *C09D 11/101* (2013.01); *B41J 2/17503* (2013.01); *B41M 5/0023* (2013.01); *C07C 69/78* (2013.01); *C07C 271/22* (2013.01); *C09D 11/00* (2013.01); *C07C 2601/16* (2017.05)

(58) Field of Classification Search
CPC ................................................... C09D 11/101
USPC ........................................................... 347/85
See application file for complete search history.

(56) References Cited

U.S. PATENT DOCUMENTS

| | | |
|---|---|---|
| 2011/0224324 A1 | 9/2011 | Loccufier et al. |
| 2017/0253680 A1 | 9/2017 | Yamada |
| 2017/0260405 A1 | 9/2017 | Kumai et al. |
| 2017/0267879 A1 | 9/2017 | Kohzuki et al. |
| 2017/0327705 A1 | 11/2017 | Yamada |
| 2018/0333909 A1 | 11/2018 | Arita et al. |
| 2019/0023924 A1 | 1/2019 | Yamada |
| 2019/0100667 A1 | 4/2019 | Miyaake et al. |
| 2019/0256727 A1 | 8/2019 | Kumai et al. |
| 2019/0270901 A1 | 9/2019 | Fujii et al. |
| 2019/0270903 A1 | 9/2019 | Kohzuki et al. |
| 2019/0284416 A1 | 9/2019 | Asami et al. |
| 2020/0010662 A1 | 1/2020 | Hiraoka et al. |

FOREIGN PATENT DOCUMENTS

| | | |
|---|---|---|
| EP | 1 616 921 B1 | 10/2007 |
| JP | 2005-104849 | 4/2005 |
| JP | 2007-204543 | 8/2007 |
| JP | 2013-522445 | 6/2013 |
| WO | WO2010/069758 A1 | 6/2010 |
| WO | WO2011/119272 A2 | 9/2011 |

*Primary Examiner* — Taofiq A Solola
(74) *Attorney, Agent, or Firm* — Grüneberg and Myers PLLC

(57) ABSTRACT

An active-energy-ray-polymerizable initiator having a structure represented by the following general formula (1) is provided.

General Formula (1)

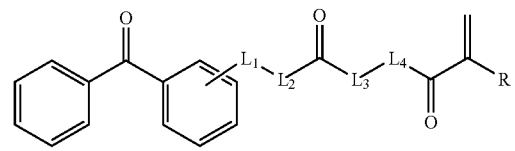

In general formula (1), $L_1$ represents —C(=O)—O— (binding to $L_2$ side) or —O—, $L_2$ represents —O(CH$_2$)$_p$-(binding to $L_1$ side), —(OC$_2$H$_4$)$_n$-(binding to $L_1$ side), or —(OC$_3$H$_6$)$_m$-(binding to $L_1$ side), where p represents an integer of 2 to 16, n represents an integer of 2 to 12, and m represents 2 or 3, $L_3$ represents a direct binding or —NH—, $L_4$ represents —OC$_2$H$_4$-(binding to $L_3$ side) or —(OC$_2$H$_4$)$_2$-(binding to $L_3$ side), and R represents —H or —CH$_3$.

9 Claims, 2 Drawing Sheets

ACTIVE-ENERGY-RAY-POLYMERIZABLE INITIATOR, ACTIVE-ENERGY-RAY-POLYMERIZABLE COMPOSITION, ACTIVE-ENERGY-RAY-POLYMERIZABLE INK, INK STORAGE CONTAINER, IMAGE FORMING METHOD, AND IMAGE FORMING APPARATUS

CROSS-REFERENCE TO RELATED APPLICATIONS

This patent application is based on and claims priority pursuant to 35 U.S.C. § 119(a) to Japanese Patent Application No. 2019-033066, filed on Feb. 26, 2019, in the Japan Patent Office, the entire disclosure of which is incorporated by reference herein.

BACKGROUND

Technical Field

The present invention relates to an active-energy-ray-polymerizable initiator, an active-energy-ray-polymerizable composition, an active-energy-ray-polymerizable ink, an ink storage container, an image forming method, and an image forming apparatus.

Description of the Related Art

An active-energy-ray-polymerizable composition is irradiated with a radioactive ray such as electron beam (EB) or ultraviolet ray (UV) to generate e.g. free radicals, and a radically polymerizable compound is polymerized by the generated free radicals to obtain a polymerization product. That means, the active-energy-ray-polymerizable composition requires two functions: a free radical generation function and a radical polymerization function.

Generally, the free radical generation function is expressed by a photoinitiator, and the radical polymerization function is expressed by a compound such as a radical polymerizable monomer or macromer having an unsaturated double bond. That means, the active-energy-ray-polymerizable composition contains at least two types of compounds: the photoinitiator and the polymerizable compound.

When a polymerization product obtained from an active-energy-ray-polymerizable composition is used for a label or a package for food, dental treatment, nail decoration, or the like, it is significant to prevent a low-molecular-weight compound having a molecular weight of about 1000 or less from leaving from the polymerization product and from moving to a contact object, from the viewpoint of safety.

The photoinitiator and the unreacted radically polymerizable monomer are objects to be prevented from leaving and moving. As a preventive measure, a method using a branched high-molecular-weight polyfunctional initiator has been proposed.

In addition, a polymerizable photoinitiator having a free radical generation function and a radical polymerization function has been proposed. For example, a polymerizable photoinitiator obtained by reacting a photoinitiator having at least one hydroxyl group with a special monomer in the presence of a catalyst, which needs neither isolation nor purification, has been proposed.

SUMMARY

In accordance with some embodiments of the present invention, an active-energy-ray-polymerizable initiator having a structure represented by the following general formula (1) is provided.

General Formula (1)

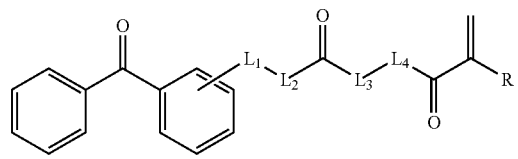

In general formula (1), $L_1$ represents —C(=O)—O— (binding to $L_2$ side) or —O—, $L_2$ represents —O(CH$_2$)$_p$- (binding to $L_1$ side), —(OC$_2$H$_4$)$_n$-(binding to $L_1$ side), or —(OC$_3$H$_6$)$_m$— (binding to $L_1$ side), where p represents an integer of 2 to 16, n represents an integer of 2 to 12, and m represents 2 or 3, $L_3$ represents a direct binding or —NH—, $L_4$ represents —OC$_2$H$_4$-(binding to $L_3$ side) or —(OC$_2$H$_4$)$_2$-(binding to $L_3$ side), and R represents —H or —CH$_3$.

BRIEF DESCRIPTION OF THE DRAWINGS

The aforementioned and other aspects, features, and advantages of the present disclosure would be better understood by reference to the following detailed description when considered in connection with the accompanying drawings, wherein.

Figure 1:
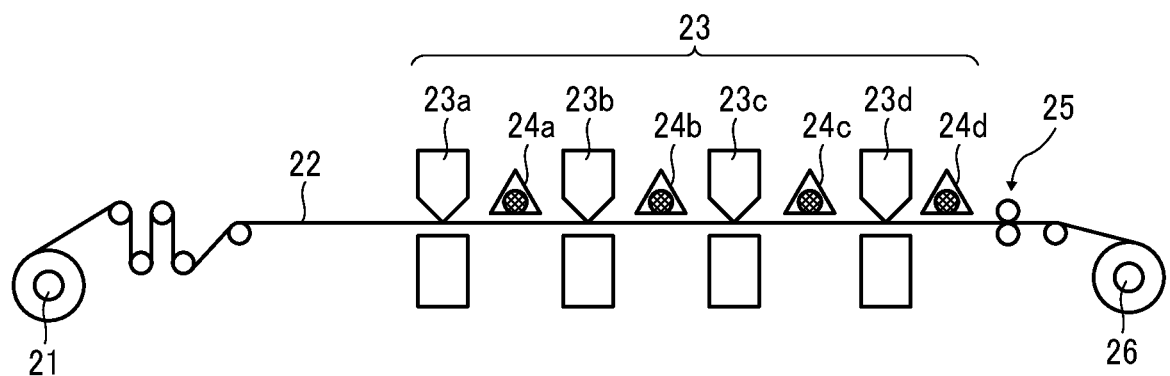
FIG. 1 is a schematic diagram illustrating an image forming apparatus according to an embodiment of the present invention.

The accompanying drawings are intended to depict embodiments of the present disclosure and should not be interpreted to limit the scope thereof. The accompanying drawings are not to be considered as drawn to scale unless explicitly noted.

DETAILED DESCRIPTION OF EMBODIMENTS

In describing embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner and achieve similar results.

Although the embodiments are described with technical limitations with reference to the attached drawings, such description is not intended to limit the scope of the disclosure and all of the components or elements described in the embodiments of this disclosure are not necessarily indispensable.

Referring now to the drawings, embodiments of the present disclosure are described below. In the drawings for explaining the following embodiments, the same reference codes are allocated to elements (members or components)

having the same function or shape and redundant descriptions thereof are omitted below.

Embodiments of the present invention provide an active-energy-ray-polymerizable initiator that exhibits an excellent polymerization speed in response to an active-energy-ray and is sufficiently prevented from leaving from a polymerization product or moving to a contact object.

Hereinafter, embodiments of the present invention will be explained. However, the present invention is not be limited to the following embodiments.

The active-energy-ray-polymerizable initiator according to an embodiment of the present invention has a structure represented by the following general formula (1).

General Formula (1)

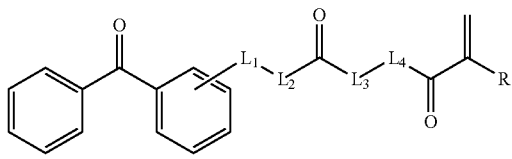

In general formula (1), $L_1$ represents —C(=O)—O— (binding to $L_2$ side) or —O—, $L_2$ represents —O(CH$_2$)$_p$- (binding to $L_1$ side), —(OC$_2$H$_4$)$_n$-(binding to $L_1$ side), or —(OC$_3$H$_6$)$_m$— (binding to $L_1$ side), where p represents an integer of 2 to 16, n represents an integer of 2 to 12, and m represents 2 or 3, $L_3$ represents a direct binding or —NH—, $L_4$ represents —OC$_2$H$_4$-(binding to $L_3$ side) or —(OC$_2$H$_4$)$_2$-(binding to $L_3$ side), and R represents —H or —CH$_3$.

In the active-energy-ray-polymerizable initiator having the structure represented by general formula (1), the benzophenone moiety absorbs light, so that hydrogen is drawn from the initiator itself or a second compound to generate free radicals. In addition, the acrylate or methacrylate moiety in general formula (1) polymerizes by the generated free radicals to provide a polymerization product.

Since the benzophenone moiety tends to draw hydrogen from a hydrocarbon adjacent to nitrogen atom, $L_3$ in general formula (1) preferably represents —NH—. In addition, for reducing volatile organic compounds or providing water solubility without using volatile organic compounds from an aspect of a usage environment, $L_2$ in general formula (1) is preferably —(C$_2$H$_4$O)$_n$—, and n is preferably an integer of 3 to 12.

The active-energy-ray-polymerizable composition according to an embodiment of the present invention includes at least the active-energy-ray-polymerizable initiator having the structure represented by general formula (1), and common substances corresponding to desired characteristics of the polymerization product. Examples of the common substances include, but are not limited to, a polymerizable monomer, a polymerization initiator, an organic solvent, water, a surfactant, and a resin.

In the active-energy-ray-polymerizable composition according to an embodiment of the present invention, a content of the active-energy-ray-polymerizable initiator having the structure represented by general formula (1) may be appropriately determined depending on an intended purpose or the like of the composition, but is preferably 1 to 55% by mass, more preferably 30 to 55% by mass.

As the polymerizable monomer, the following (meth) acrylates, (meta)acrylamides, vinyl ethers, and the like can be used in combination.

Examples of the polymerizable monomer include, but are not limited to, ethyleneglycol di(meth)acrylate, hydroxypivalic acid neopentylglycol di(meth) acrylate, γ-butyrolactone acrylate, isobornyl (meth)acrylate, formalated trimethylolpropane mono(meth)acrylate, polytetramethyleneglycol di(meth)acrylate, trimethylolpropane (meth)acrylic acid benzoate, triethyleneglycol di(meth)acrylate, tetraethyleneglycol di(meth)acrylate, polyethyleneglycol diacrylate [CH$_2$=CH—CO—(OC$_2$H$_4$)$_n$—OCOCH=CH$_2$ (n≈4)], polyethyleneglycol diacrylate [CH$_2$=CH—CO—(OC$_2$H$_4$)$_n$—OCOCH=CH$_2$ (n≈9)], polyethyleneglycol diacrylate [CH$_2$=CH—CO—(OC$_2$H$_4$)$_n$—OCOCH=CH$_2$ (n≈14)], polyethyleneglycol diacrylate [CH$_2$=CH—CO—(OC$_2$H$_4$)$_n$—OCOCH=CH$_2$ (n≈23)], dipropyleneglycol di(meth)acrylate, tripropyleneglycol di(meth)acrylate, polypropyleneglycol dimethacrylate [CH$_2$=C(CH$_3$)—CO—(OC$_3$H$_6$)$_n$—OCOC(CH$_3$)=CH$_2$ (n≈7)], 1,3-butanediol di(meth)acrylate, 1,4-butanediol diacrylate, 1,6-hexanediol di(meth)acrylate, 1,9-nonanediol di(meth)acrylate, neopentylglycol diacrylate, tricyclodecanedimethanol diacrylate, propylene oxide-modified bisphenol A di(meth)acrylate, polyethyleneglycol di(meth)acrylate, dipentaerythritol hexa(meth)acrylate, (meth)acryloylmorpholine, propylene oxide-modified tetramethylolmethane tetra(meth)acrylate, dipentaerythritolhydroxy penta(meth)acrylate, caprolactone-modified dipentaerythritolhydroxy penta(meth)acrylate, ditrimethylolpropane tetra(meth)acrylate, pentaerythritol tetra(meth)acrylate, trimethylolpropane triacrylate, ethylene oxide-modified trimethylolpropane tri(meth)acrylate, propylene oxide-modified trimethylolpropane tri(meth)acrylate, caprolactone-modified trimethylolpropane tri(meth)acrylate, pentaerythritol tri(meth)acrylate, tris(2-hydroxyethyl)isocyanurate tri(meth)acrylate, neopentylglycol diacrylate, ethoxylated neopentylglycol di(meth)acrylate, propylene oxide-modified neopentylglycol di(meth)acrylate, propylene oxide-modified glyceryl tri(meth)acrylate, polyester di(meth)acrylate, polyester tri(meth)acrylate, polyester tetra(meth)acrylate, polyester penta(meth)acrylate, polyester poly(meth)acrylate, polyurethane di(meth)acrylate, polyurethane tri(meth)acrylate, polyurethane tetra(meth)acrylate, polyurethane penta(meth)acrylate, polyurethane poly(meth)acrylate, 2-hydroxypropyl (meth)acrylamide, N-vinylcaprolactam, N-vinylpyrrolidone, N-vinylformamide, cyclohexanedimethanol monovinyl ether, cyclohexanedimethanol divinyl ether, hydroxyethyl vinyl ether, diethyleneglycol monovinyl ether, diethyleneglycol divinyl ether, dicyclopentadiene vinyl ether, tricyclodecane vinyl ether, benzyl vinyl ether, and ethyloxetanemethyl vinyl ether.

In the active-energy-ray-polymerizable composition according to an embodiment of the present invention, a content of the polymerizable monomer may be appropriately determined depending on an intended purpose or the like of the composition, but is preferably 25 to 99% by mass, more preferably 25 to 75% by mass.

The active-energy-ray-polymerizable composition according to an embodiment of the present invention may contain a polymerization initiator other than the active-energy-ray-polymerizable initiator having the structure represented by general formula (1). The polymerization initiator may be any polymerization initiator which can produce active species such as radicals and cations by energy of the active energy ray and initiate polymerization of polymerizable compounds (monomers and oligomers). As such a polymerization initiator, a known radical polymerization initiator, cationic polymerization initiator, base producing agent, and the like can be used alone or in combination, and above all, the radical polymerization initiator is preferably used. Examples of the radical polymerization initiator include, but are not limited to, an aromatic ketone, an acylphosphine oxide compound, an aromatic onium salt compound, an organic peroxide, a thio compound (such as thioxanthone compound and thiophenyl group-containing compound), a hexaaryl biimidazole compound, a ketoxime ester compound, a borate compound, an azinium compound, a metallocene compound, an active ester compound, a compound having a carbon-halogen bond, and an alkylamine compound.

In the active-energy-ray-polymerizable composition according to an embodiment of the present invention, a content of the polymerization initiator other than the active-energy-ray-polymerizable initiator having the structure represented by general formula (1) may be appropriately determined depending on an intended purpose or the like of the composition, but is e.g. 0 to 5% by mass.

In addition to the above polymerization initiators, a polymerization accelerator (sensitizer) can be used in combination. The polymerization accelerator is not particularly limited, but is preferably e.g. an amine compound such as trimethylamine, methyldimethanolamine, triethanolamine, p-diethylaminoacetophenone, p-dimethylaminobenzoic acid ethyl ester, p-dimethylaminobenzoic acid 2-ethylhexyl ester, N,N-dimethylbenzyl amine, and 4,4'-bis(diethylamino)benzophenone. A content of the polymerization accelerator may be appropriately set depending on a type and an amount of a polymerization initiator to be used.

The active-energy-ray-polymerizable composition according to an embodiment of the present invention may contain an organic solvent. As the organic solvent, a general-purpose water-insoluble organic solvent such as toluene and ethyl acetate can be used. In addition, since the active-energy-ray-polymerizable initiator according to an embodiment of the present invention exhibits water-solubility by introduction of an ethylene oxide group, a hydrophilic organic solvent can be used in combination.

Specific examples of the water-soluble organic solvent include, but are not limited to, a polyhydric alcohol such as ethyleneglycol, diethyleneglycol, 1,2-propanediol, 1,3-propanediol, 1,2-butanediol, 1,3-butanediol, 1,4-butanediol, 2,3-butanediol, 3-methyl-1,3-butanediol, triethyleneglycol, polyethyleneglycol, polypropyleneglycol, 1,2-pentanediol, 1,3-pentanediol, 1,4-pentanediol, 2,4-pentanediol, 1,5-pentanediol, 1,2-hexanediol, 1,6-hexanediol, 1,3-hexanediol, 2,5-hexanediol, 1,5-hexanediol, glycerol, 1,2,6-hexanetriol, 2-ethyl-1,3-hexanediol, ethyl-1,2,4-butanetriol, 1,2,3-butanetriol, 2,2,4-trimethyl-1,3-pentanediol, and 3-methyl-1,3,5-pentanetriol; a polyhydric alcohol alkyl ether such as ethyleneglycol monoethyl ether, ethyleneglycol monobutyl ether, diethyleneglycol monomethyl ether, diethyleneglycol monoethyl ether, di ethyleneglycol monobutyl ether, tetraethyleneglycol monomethyl ether, and propyleneglycol monoethyl ether; a polyhydric alcohol aryl ether such as ethyleneglycol monophenyl ether, and ethyleneglycol monobenzyl ether; a nitrogen-containing heterocyclic compound such as 2-pyrrolidone, N-methyl-2-pyrrolidone, N-hydroxyethyl-2-pyrrolidone, 1,3-dimethyl-2-imidazolidinone, ε-caprolactam, and γ-butyrolactone; an amide such as formamide, N-methylformamide, N,N-dimethylformamide, 3-methoxy-N,N-dimethylpropionamide, and 3-butoxy-N,N-dimethylpropionamide; an amine such as monoethanolamine, diethanolamine, and triethylamine; a sulfur-containing compound such as dimethylsulfoxide, sulfolane, and thiodiethanol; propylene carbonate; and ethylene carbonate.

In the active-energy-ray-polymerizable composition according to an embodiment of the present invention, a content of the organic solvent may be appropriately determined depending on an intended purpose or the like of the composition, but is e.g. 10 to 60% by mass.

The active-energy-ray-polymerizable composition according to an embodiment of the present invention may contain a surfactant.

Examples of the surfactant include, but are not limited to, a silicone-based surfactant, a fluorine-based surfactant, and a nonionic surfactant.

The silicone-based surfactant is not particularly limited, and can be appropriately selected depending on an intended purpose. Particularly, a silicone-based surfactant that is not decomposed even at a high pH is preferable, and examples thereof include, but are not limited to, a side-chain-modified polydimethylsiloxane, a both-end-modified polydimethylsiloxane, a one-end-modified polydimethylsiloxane, and a side-chain-both-end-modified polydimethylsiloxane. Those having a polyoxyethylene group or a polyoxyethylenepolyoxypropylene group as the modifying group are particularly preferable because of suitable characteristics as an aqueous surfactant. In addition, as the silicone-based surfactant, a polyether-modified silicone-based surfactant can also be used, and examples of the silicone-based surfactant includes, but are not limited to, a compound in which a polyalkylene oxide structure is introduced into a side chain of Si of dimethylsiloxane.

As the fluorine-based surfactant, e.g. a perfluoroalkylsulfonic acid compound, a perfluoroalkylcarboxylic acid compound, a perfluoroalkyl phosphate compound, a perfluoroalkyl ethylene oxide adduct, and a polyoxyalkylene ether polymer compound having a perfluoroalkyl ether group at a side chain are particularly preferable because of low foamability. Examples of the perfluoroalkylsulfonic acid compound include, but are not limited to, a perfluoroalkylsulfonic acid, and perfluoroalkylsulfonate. Examples of the perfluoroalkylcarboxylic acid compound include, but are not limited to, a perfluoroalkylcarboxylic acid, and a perfluoroalkylcarboxylate. Examples of the polyoxyalkylene ether polymer compound having the perfluoroalkyl ether group at a side chain include, but are not limited to, a sulfate ester salt of polyoxyalkylene ether polymer having a perfluoroalkyl ether group at a side chain, and a salt of polyoxyalkylene ether polymer having a perfluoroalkyl ether group at a side chain. Examples of a counter ion of the salts in these fluorine-based surfactants include, but are not limited to, Li, Na, K, $NH_4$, $NH_3CH_2CH_2OH$, $NH_2(CH_2CH_2OH)_2$, and $NH(CH_2CH_2OH)_3$.

In the active-energy-ray-polymerizable composition according to an embodiment of the present invention, a content of the surfactant may be appropriately determined depending on an intended purpose or the like of the composition, but is e.g. 1 to 5% by mass.

The active-energy-ray-polymerizable composition according to an embodiment of the present invention may contain a resin.

A type of the resin is not particularly limited, and can be appropriately selected depending on an intended purpose. Examples of the resin include, but are not limited to, an urethane resin, a polyester resin, an acrylic resin, a vinyl-acetate-based resin, a styrene-based resin, a butadiene-based resin, a styrene-butadiene-based resin, a vinyl-chloride-based resin, an acryl-styrene-based resin, and an acryl-silicone-based resin.

Resin particles made of these resins may also be used. An ink can be obtained by mixing a material such as a colorant and an organic solvent with a resin particle in a state of a resin emulsion in which the resin particle is dispersed in water as a dispersion medium. As the resin particle, an appropriately synthesized resin may be used, or a commercially available product may be used. In addition, these resin particles may be used alone or in combination.

In the active-energy-ray-polymerizable composition according to an embodiment of the present invention, a content of the resin may be appropriately determined depending on an intended purpose or the like of the composition, but is e.g. 10 to 90% by mass.

The active-energy-ray-polymerizable composition according to an embodiment of the present invention can be prepared using the aforementioned various components. Devices and conditions for preparation are not particularly limited, but for example, the active-energy-ray-polymerizable composition can be prepared by a process that a polymerizable monomer, a pigment, a dispersant, and the like are subjected to a dispersing machine such as a ball mill, a kitty mill, a disk mill, a pin mill, and a DYNO-MILL, and dispersed to prepare a pigment liquid dispersion, and further a polymerizable monomer, an initiator, a polymerization inhibitor, a surfactant, and the like are blended into the pigment liquid dispersion.

The active energy ray applied to the active-energy-ray-polymerizable initiator according to an embodiment of the present invention is not limited as long as the active energy ray can provide an energy required for advancing a polymerization reaction. Examples thereof include, but are not limited to, ultraviolet ray, electron beam, α-ray, β-ray, γ-ray, and X-ray. In the case of ultraviolet irradiation, mercury-free ultraviolet irradiation is eagerly desired from the viewpoint of environmental protection, and replacement with a GaN-based semiconductor ultraviolet light-emitting device is industrially and environmentally very useful. Furthermore, ultraviolet light-emitting diode (UV-LED) and ultraviolet laser diode (UV-LD) are preferable as ultraviolet light sources because of small size, long life, high efficiency, and low cost.

The active-energy-ray-polymerizable ink according to an embodiment of the present invention contains the active-energy-ray-polymerizable composition, a colorant, and optionally other components.

<Colorant>

The colorant is not particularly limited, and a pigment and a dye can be used. As the pigment, an inorganic pigment or an organic pigment can be used. These pigments may be used alone or in combination. Also, a mixed crystal may be used.

As the pigment, e.g. a black pigment, a yellow pigment, a magenta pigment, a cyan pigment, a white pigment, a green pigment, an orange pigment, a glossy color pigment such as gold and silver, a metallic pigment, and the like can be used.

As the inorganic pigment, titanium oxide, iron oxide, calcium carbonate, barium sulfate, aluminum hydroxide, barium yellow, cadmium red, and chrome yellow, as well as a carbon black produced by a known method such as a contact method, a furnace method, and a thermal method can be used.

As the organic pigment, an azo pigment, a polycyclic pigment (e.g. a phthalocyanine pigment, a perylene pigment, a perinone pigment, an anthraquinone pigment, a quinacridone pigment, a dioxazine pigment, an indigo pigment, a thioindigo pigment, an isoindolinone pigment, a quinophthalone pigment, and the like), a dye chelate (e.g. a basic dye type chelate, an acidic dye type chelate, and the like), a nitro pigment, a nitroso pigment, aniline black, and the like can be used. Among them, a pigment having a high affinity for the solvent is preferably used. In addition, a hollow resin particle and a hollow inorganic particle can also be used.

Specific examples of the black pigment include, but are not limited to, a carbon black (Color Index (C. I.) Pigment Black 7) such as furnace black, lamp black, acetylene black, and channel black, a metal such as copper, iron (C. I. Pigment Black 11), and titanium oxide, and an organic pigment such as aniline black (C. 1. Pigment Black 1).

Furthermore, examples of the color pigment include, but are not limited to, C. I. Pigment Yellow 1, 3, 12, 13, 14, 17, 24, 34, 35, 37, 42 (yellow iron oxide), 53, 55, 74, 81, 83, 95, 97, 98, 100, 101, 104, 108, 109, 110, 117, 120, 138, 150, 153, 155, 180, 185, and 213, C. I. Pigment Orange 5, 13, 16, 17, 36, 43, and 51, C. I. Pigment Red 1, 2, 3, 5, 17, 22, 23, 31, 38, 48:2, 48:2 (Permanent Red 2B (Ca)), 48:3, 48:4, 49:1, 52:2, 53:1, 57:1 (Brilliant Carmine 6B), 60:1, 63:1, 63:2, 64:1, 81, 83, 88, 101 (Rouge), 104, 105, 106, 108 (Cadmium Red), 112, 114, 122 (Quinacridone Magenta), 123, 146, 149, 166, 168, 170, 172, 177, 178, 179, 184, 185, 190, 193, 202, 207, 208, 209, 213, 219, 224, 254, and 264, C. I. Pigment Violet 1 (Rhodamine Lake), 3, 5:1, 16, 19, 23, and 38, C. 1. Pigment Blue 1, 2, 15 (Phthalocyanine Blue), 15:1, 15:2, 15:3, 15:4 (Phthalocyanine Blue), 16, 17:1, 56, 60, and 63, and C. I. Pigment Green 1, 4, 7, 8, 10, 17, 18, and 36.

The dye is not particularly limited. For the dye, an acidic dye, a direct dye, a reactive dye, and a basic dye may be used alone or in combination.

Examples of the dye include, but are not limited to, C. I. Acid Yellow 17, 23, 42, 44, 79, and 142, C. I. Acid Red 52, 80, 82, 249, 254, and 289, C. I. Acid Blue 9, 45, and 249, C. I. Acid Black 1, 2, 24, and 94, C. I. Food Black 1 and 2, C. I. Direct Yellow 1, 12, 24, 33, 50, 55, 58, 86, 132, 142, 144, and 173, C. I. Direct Red 1, 4, 9, 80, 81, 225, and 227, C. I. Direct Blue 1, 2, 15, 71, 86, 87, 98, 165, 199, and 202, C. 1. Direct Black 19, 38, 51, 71, 154, 168, 171, and 195, C. I. Reactive Red 14, 32, 55, 79, and 249, and C. I. Reactive Black 3, 4, and 35.

A content of the colorant in the ink is preferably 0.1% by mass or more and 15% by mass or less, more preferably 1% by mass or more and 10% by mass or less, from the viewpoints of improved image density, and good fixity and discharge stability.

For the purpose of dispersing the pigment in an ink, a method of introducing a hydrophilic functional group into a pigment to obtain a self-dispersible pigment, a method of coating a surface of a pigment with a resin and dispersing the pigment, a method of dispersing the pigment using a dispersant, or the like may be used.

In the method of introducing the hydrophilic functional group into the pigment to obtain the self-dispersible pigment, a self-dispersible pigment may be prepared by adding a functional group such as a sulfone group and a carboxyl group to a pigment (e.g. carbon) to allow the pigment to be dispersed in water In the method of coating the surface of the pigment with the resin and dispersing the pigment, a pigment that can be dispersed in water may be prepared by incorporating the pigment by a microcapsule. This pigment can be rephrased as a resin-coated pigment. In this case, not all the pigments blended in the ink need to be coated with the resin, and uncoated pigments or partially coated pigments may be dispersed in the ink as long as the effect of the present invention is not impaired.

Examples of the method of dispersing the pigment using the dispersant include, but are not limited to, a method of dispersing the pigment using a known low-molecular type dispersant or high-molecular type dispersant typified by surfactants.

As the dispersant, e.g. an anionic surfactant, a cationic surfactant, an amphoteric surfactant, a nonionic surfactant or the like can be used depending on the pigment.

Also, RT-100 (nonionic surfactant) manufactured by TAKEMOTO OIL & FAT Co., Ltd. and formalin condensate of sodium naphthalenesulfonate can be suitably used as a dispersant. The dispersant may be used alone or in combination.

<Pigment Dispersion>

An ink can be obtained by blending materials such as water and an organic solvent with a pigment. Also, a pigment dispersion prepared by mixing a pigment with other components such as water and a dispersant can be blended with materials such as water and an organic solvent to produce an ink.

The pigment dispersion is obtained by dispersing water, a pigment, a pigment dispersant, and optionally other components, and adjusting a particle diameter of the pigment. Preferably, the dispersion is performed by a disperser.

The particle diameter of the pigment in the pigment dispersion is not particularly limited. However, the diameter of the highest-frequency particle in terms of the maximum number of particles is preferably 20 nm or more and 500 nm or less, more preferably 20 nm or more and 150 nm or less, from the viewpoints of preferable dispersion stability of the pigment, high discharge stability, and high image quality such as image density. The particle diameter of the pigment can be measured using a particle size analyzer (Nanotrac Wave-UT151, manufactured by MicrotracBEL Corp.).

A content of the pigment in the pigment dispersion is not particularly limited, and can be appropriately selected depending on the intended purpose. However, the content is preferably 0.1% by mass or more and 50% by mass or less, more preferably 0.1% by mass or more and 30% by mass or less, from the viewpoints of good discharge stability and high image density.

Preferably, the pigment dispersion is optionally filtered to remove coarse particles by a filter, a centrifuge or the like, and degassed.

The active-energy-ray-polymerizable ink according to an embodiment of the present invention may contain an antifoaming agent, an antiseptic and antifungal agent, an antirust agent, and/or a pH conditioner.

<Antifoaming Agent>

The antifoaming agent is not particularly limited. Examples of the antifoaming agent include, but are not limited to, a silicone-based antifoaming agent, a polyether-based antifoaming agent, and a fatty acid ester-based antifoaming agent. These antifoaming agents may be used alone or in combination. Above all, the silicone-based antifoaming agent is preferable from the viewpoint of excellent foam breaking effect.

<Antiseptic and Antifungal Agent>

The antiseptic and antifungal agent is not particularly limited. Examples of the antiseptic and antifungal agent include, but are not limited to, 1,2-benzisothiazolin-3-one.

<Antirust Agent>

The antirust agent is not particularly limited. Examples of the antirust agent include, but are not limited to, acidic sulfite, and sodium thiosulfate.

<pH Conditioner>

The pH conditioner is not particularly limited as long as the pH conditioner can adjust the ink to pH 7 or more. Examples of the pH conditioner include, but are not limited to, an amine such as diethanolamine and triethanolamine. The physical properties of the ink are not particularly limited, and can be appropriately selected depending on the intended purpose. For example, viscosity, surface tension, pH, and the like are preferably within the following ranges.

The viscosity of the ink at 25° C. is preferably 5 mPa·s or more and 30 mPa·s more less, more preferably 5 mPa·s or more and 25 mPa·s more less, from the viewpoints that a character printing density and a character quality are improved and good dischargeability can be obtained. Herein, the viscosity can be measured using e.g. a rotary viscometer (RE-80L manufactured by Toki Sangyo Co., Ltd). The measurement can be implemented under a measurement condition using a standard cone rotor (1°34'×R24), with a sample liquid volume of 1.2 mL, at a rotation speed of 50 rpm, and 25° C., for 3 minutes.

The surface tension of the ink is preferably 35 mN/m or less, more preferably 32 mN/m or less at 25° C. from the viewpoints that the ink can be suitably leveled on a recording medium and a time for drying the ink can be shortened.

The pH of the ink is preferably 7 to 12, more preferably 8 to 11, from the viewpoint of preventing corrosion of a metal member in contact with a liquid.

Applications of the active-energy-ray-polymerizable composition according to an embodiment of the present invention are not particularly limited, and can be appropriately selected depending on an intended purpose. Exemplary applications include, but are not limited to, a molding resin, a paint, an adhesive, an insulating material, a mold lubricant, a coating material, a sealing material, various resists, and various optical materials.

Figure 2:
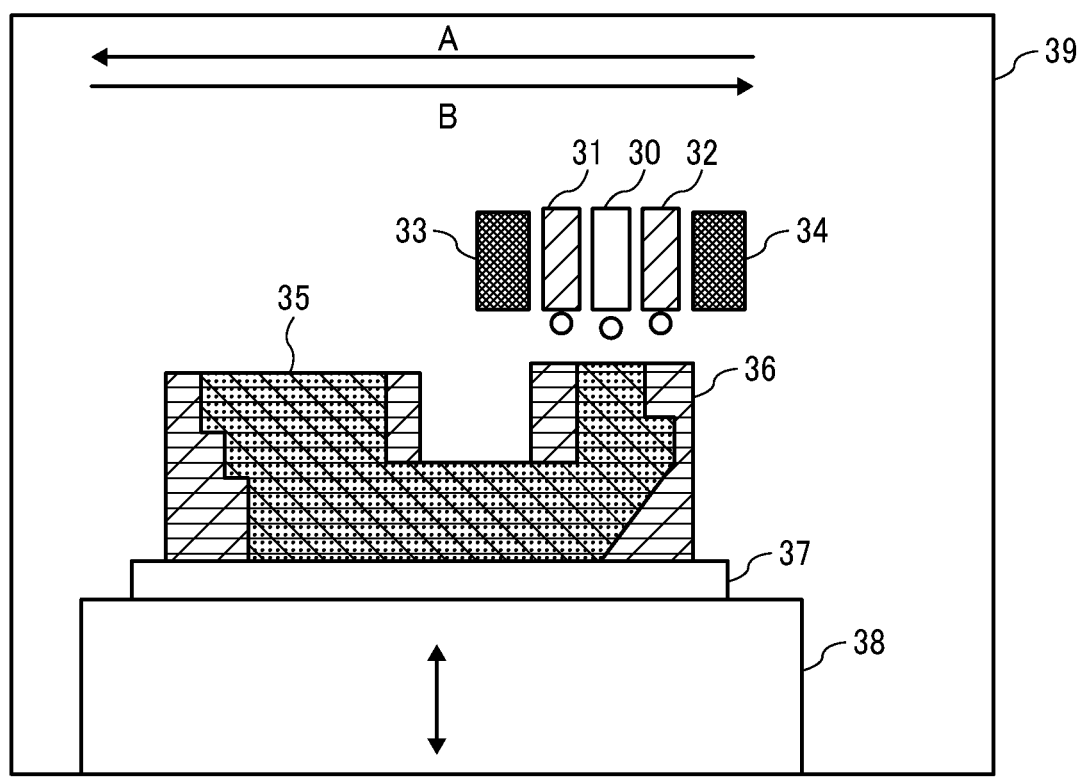
FIG. 2 is a schematic diagram illustrating another image forming apparatus according to an embodiment of the present invention.
Figure 3A:
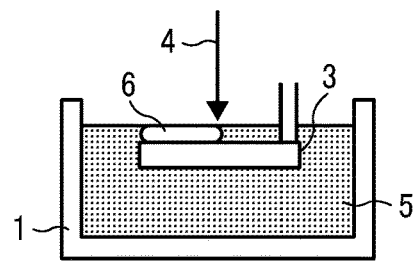
FIGS. 3A to 3D are schematic diagrams illustrating still another image forming apparatus according to an embodiment of the present invention.
Figure 3B:
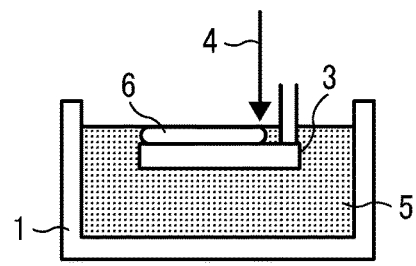
Figure 3C:
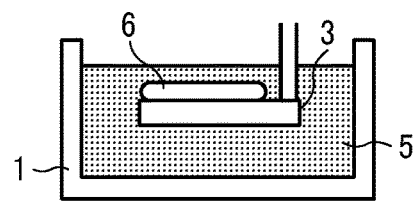
Figure 3D:
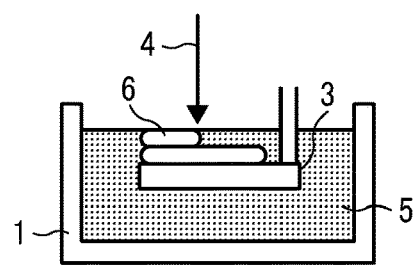

Furthermore, the active-energy-ray-polymerizable composition according to an embodiment of the present invention can be used not only as ink for forming two-dimensional texts and images, and designed coating films on various substrates, but also as a solid object forming material for forming three-dimensional objects (solid objects). This solid object forming material may be used e.g. as a binder between powder particles used in a powder laminating method for forming a solid object by repeatedly curing and laminating a powder layer, or as a solid object constituent material (model material) or a supporting member (support material) used in an additive manufacturing method (stereolithography method) as illustrated in FIG. 2 and FIG. 3. Incidentally, FIG. 2 presents a method in which the active-energy-ray-polymerizable composition according to an embodiment of the present invention is discharged to a predetermined area, and cured by irradiation with an active energy ray, these cured products are sequentially laminated to form a solid object (details will be explained later), and FIGS. 3A to 3D present a method in which a storage pool (storage section) 1 for an active-energy-ray-polymerizable composition 5 according to an embodiment of the present invention is irradiated with an active energy ray 4 to form a cured layer 6 having a predetermined shape on a movable stage 3, and the cured layers 6 are sequentially laminated to form a solid object.

As an apparatus for fabricating a solid object using the active-energy-ray-polymerizable composition according to an embodiment of the present invention, a known apparatus can be used. The apparatus is not particularly limited, and examples of the apparatus include, but are not limited to, an apparatus including a storing device, a supplying device, and a discharging device of the composition, as well as an active energy ray irradiator, and the like.

In addition, the present invention includes a cured product obtained by curing the active-energy-ray-polymerizable composition according to an embodiment of the present invention, and a formed article obtained by processing a structure in which the cured product is formed on a substrate. The formed article is obtained by subjecting the cured product or structure in e.g. a sheet shape or a film shape to processing such as heat drawing or punching. For example, the formed article is suitably used for applications such as a meter, an operation panel or the like of an automobile, an OA equipment, an electric/electronic equipment, a camera or the like, which should be formed after surface decoration.

The substrate is not particularly limited, and can be appropriately selected according to the intended purpose. Examples of the substrate include, but are not limited to, paper, thread, fiber, cloth, leather, metal, plastic, glass, wood, ceramics, or a composite material thereof. From the viewpoint of processability, the plastic substrate is preferable.

The ink storage container according to an embodiment of the present invention includes a container and the active-energy-ray-polymerizable ink stored in the container, and is suitable for the above applications. For example, the ink storage container according to an embodiment of the present invention can be used as an ink cartridge or an ink bottle, thereby it is not required to directly touch the ink during operations such as ink transportation and ink replacement, and dirt on fingers and clothing can be prevented. In addition, contamination of the ink with foreign matters such as dusts can be prevented. It is sufficient that a shape, a size, a material, and the like of the container itself are suitable for the application and usage method. Although the material is not particularly limited, it is preferable that the material is a light-shielding material not transmitting light, or the container is covered with a light-shielding sheet or the like.

The image forming method according to an embodiment of the present invention includes a step of discharging the active-energy-ray-polymerizable ink according to an embodiment of the present invention onto a recording medium to form an image.

In addition, the image forming apparatus according to an embodiment of the present invention includes an ink storage container storing the active-energy-ray-polymerizable ink according to an embodiment of the present invention, and a discharging device configured to discharge the ink stored in the ink storage container onto a recording medium.

Hereinafter, the image forming method and the image forming apparatus will be explained in detail.

For curing the active-energy-ray-polymerizable ink according to an embodiment of the present invention with the active energy ray, the image forming method includes an irradiation process for emitting the active energy ray. The image forming apparatus according to an embodiment of the present invention includes an irradiator for emitting the active-energy-ray, and a storing unit for storing the active-energy-ray-polymerizable ink according to an embodiment of the present invention. The storing unit may contain the container. Furthermore, a process and a device for discharging the active-energy-ray-polymerizable ink may be included. The discharging method is not particularly limited, but a continuous injection type method, an on-demand type method, or the like is used. Examples of the on-demand type method include, but are not limited to, a piezo method, a thermal method, and an electrostatic method.

FIG. 1 illustrates an image forming apparatus including an inkjet discharging device. Each color printing unit 23a, 23b, 23c, or 23d including an ink cartridge for each color active-energy-ray-polymerizable ink of yellow, magenta, cyan, or black and a discharging head discharges the ink to a recording medium 22 supplied from a supply roll 21. Then, the ink is cured by irradiating the ink with an active energy ray from a light source 24a, 24b, 24c, or 24d for curing the ink, to form a color image. Subsequently, the recording medium 22 is conveyed to a processing unit 25 and a printed matter winding roll 26. Each printing unit 23a, 23b, 23c, or 23d may include a heating mechanism such that the ink liquefies on an ink discharging part. In addition, a mechanism for cooling a recording medium to approximately room temperature in a contact/non-contact manner may be installed if required. Furthermore, as the inkjet recording method, it is possible to use both a serial method in which a head is moved relative to a recording medium capable of intermittently moving depending on a width of a discharging head to discharge an ink onto the recording medium, and a line method in which a recording medium is continuously moved and an ink is discharged onto the recording medium from a head held in a certain position.

The recording medium 22 is not particularly limited, but examples of the recording medium 22 include, but are not limited to, paper, film, ceramics, glass, metal, and a composite material thereof. The recording medium 22 may be formed into a sheet shape. In addition, the recording medium 22 may have either a configuration capable of one-side printing alone or a configuration capable of both-side printing. Not only materials used as general recording media but also cardboard, building materials such as wallpaper and floor material, concrete, fabric for a clothing such as a T-shirt, textile, leather, and the like can be used as appropriate.

Furthermore, after the active-energy-ray radiation from the light source 24a, 24b, and 24c is weakened or omitted and the plurality of colors are printed, the active energy ray may be emitted from the light source 24d. Thereby, energy saving and low cost can be achieved.

Examples of the recorded matter recorded with the ink according to an embodiment of the present invention include printed smooth surfaces such as normal paper and resin film, as well as printed rugged surfaces, and printed surfaces including various materials such as metal and ceramic. In addition, an image partially having a three-dimensional effect (two-dimensional and three-dimensional image) and a solid matter can be formed by laminating two-dimensional images.

FIG. 2 is a schematic diagram illustrating another image forming apparatus (three-dimensional object forming apparatus) according to an embodiment of the present invention. In an image forming apparatus 39 in FIG. 2, using a head unit (movable in AB direction) having arranged inkjet heads, a first active-energy-ray-polymerizable ink is discharged from an object discharge head unit 30, a second active-energy-ray-polymerizable ink having a different composition from that of the first active-energy-ray-polymerizable ink is discharged from support discharge head units 31 and 32, and these inks are laminated while being cured with adjacent ultraviolet irradiators 33 and 34. More specifically, for example, the second active-energy-ray-polymerizable ink is discharged onto an object supporting substrate 37 from the support discharge head units 31 and 32, and solidified by active-energy-ray irradiation to form a first support layer having a reservoir. Then the first active-energy-ray-polymerizable ink is discharged onto the reservoir from the object discharge head unit 30, and solidified by active-energy-ray irradiation to form a first object layer. This process is repeated multiple times in accordance with the number of laminations while lowering a vertically-movable stage 38, so that the support layer and the object layer are laminated to produce a solid object 35. Subsequently, a support laminating portion 36 is removed if required. In FIG. 2, although just one object discharge head unit 30 is illustrated, two or more object discharge head units 30 can be installed.

EXAMPLES

Hereinafter, the present invention will be further explained with reference to Examples and Comparative Examples, but the present invention is not limited to the following examples.
<<Preparation of Active-Energy-Ray-Polymerizable Initiator>>

Example 1

To 11.50 g (250 mmol) of ethyleneglycol (manufactured by Tokyo Chemical Industry Co., Ltd.), 0.49 g (5 mmol) of sulfuric acid (manufactured by KANTO CHEMICAL CO., INC.) was added, to which 11.31 g (50 mmol) of 2-benzoylbenzoic acid (Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 8.80 g of 2-benzoyl-(2-hydroxyethyl benzoate) (intermediate 1).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 6.76 g (25 mmol) of 2-benzoyl-(2-hydroxyethyl benzoate) (intermediate 1), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 13.50 g of active-energy-ray-polymerizable initiator (JK-1) according to an embodiment of the present invention having a structure represented by formula (1).

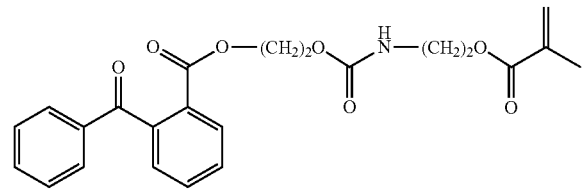

Example 2

After 29.50 g (250 mmol) of 1,6-hexanediol was heated until it melted, 0.49 g (5 mmol) of sulfuric acid was added. To the mixture, 11.31 g (50 mmol) of 2-benzoylbenzoic acid was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 11.30 g of 2-benzoyl-(6-hydroxyhexyl benzoate) (intermediate 2).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 8.16 g (25 mmol) of 2-benzoyl-(2-hydroxyhexyl benzoate) (intermediate 2), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 7.80 g of active-energy-ray-polymerizable initiator (JK-2) according to an embodiment of the present invention having a structure represented by formula (2).

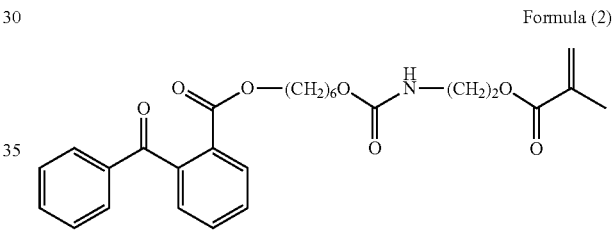

Example 3

After 64.60 g (250 mmol) of 1,16-hexadecanediol was heated until it melted, 0.49 g (5 mmol) of sulfuric acid was added. To the mixture, 11.31 g (50 mmol) of 2-benzoylbenzoic acid was added little by little while stirring, then heated to 120° C., and stirred for 4 hours. The mixture was cooled to room temperature, a resulting reaction solution was neutralized with a sodium hydrogencarbonate aqueous solution, to which 120 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 14.30 g of 2-benzoyl-(16-hydroxyhexadecane benzoate) (intermediate 3).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 11.67 g (25 mmol) of 2-benzoyl-(2-hydroxyhexadecane benzoate), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 10.70 g of active-energy-ray-polymerizable initiator (JK-3) according to an embodiment of the present invention having a structure represented by formula (3).

Formula (3)

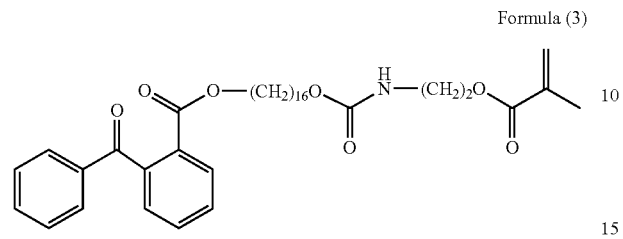

Example 4

To 15 mL of super dehydrated methylene chloride (manufactured by Wako Pure Chemical Industries, Ltd.), 3.53 g (25 mmol) of 2-isocyanatoethyl acrylate (Karenz AOI, manufactured by SHOWA DENKO K.K.), 8.16 g (25 mmol) of 2-benzoyl-(2-hydroxyhexyl benzoate) (intermediate 2), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 7.20 g of active-energy-ray-polymerizable initiator (JK-4) according to an embodiment of the present invention having a structure represented by formula (4).

Formula (4)

Example 5

To 26.50 g (250 mmol) of diethyleneglycol (manufactured by Tokyo Chemical Industry Co., Ltd.), 0.49 g (5 mmol) of sulfuric acid (manufactured by KANTO CHEMICAL CO., INC.) was added, to which 11.31 g (50 mmol) of 2-benzoylbenzoic acid (Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 10.80 g of intermediate 4 having a structure represented by intermediate formula (4).

Intermediate Formula (4)

Intermediate 4

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 7.86 g (25 mmol) of intermediate 4, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 7.20 g of active-energy-ray-polymerizable initiator (JK-5) according to an embodiment of the present invention having a structure represented by formula (5).

Formula (5)

Example 6

After 48.60 g (250 mmol) of tetraethyleneglycol (manufactured by Tokyo Chemical Industry Co., Ltd.) was heated until it melted, 0.49 g (5 mmol) of sulfuric acid (manufactured by KANTO CHEMICAL CO., INC.) was added. To the mixture, 11.31 g (50 mmol) of 2-benzoylbenzoic acid (manufactured by Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 12.50 g of intermediate 5 having a structure represented by intermediate formula (5).

Intermediate Formula (5)

Intermediate 5

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 10.06 g (25 mmol) of intermediate 5, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 8.60 g of active-energy-ray-polymerizable initiator (JK-6) according to an embodiment of the present invention having a structure represented by formula (6).

Formula (6)

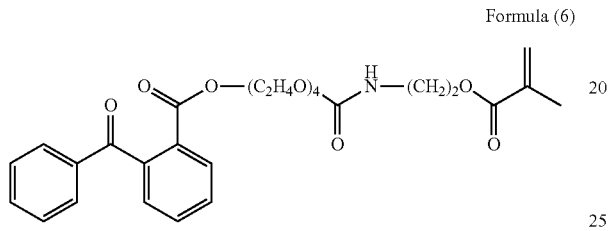

Example 7

After 136.6 g (250 mmol) of dodecaethyleneglycol (manufactured by Tokyo Chemical Industry Co., Ltd.) was heated until it melted, 0.49 g (5 mmol) of sulfuric acid (manufactured by KANTO CHEMICAL CO., INC.) was added. To the mixture, 11.31 g (50 mmol) of 2-benzoylbenzoic acid (manufactured by Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 150 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 12.50 g of intermediate 6 having a structure represented by intermediate formula (6).

Intermediate Formula (6)

Intermediate 6

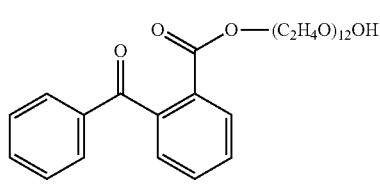

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 18.88 g (25 mmol) of intermediate 5, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 14.00 g of active-energy-ray-polymerizable initiator (JK-7) according to an embodiment of the present invention having a structure represented by formula (7).

Formula (7)

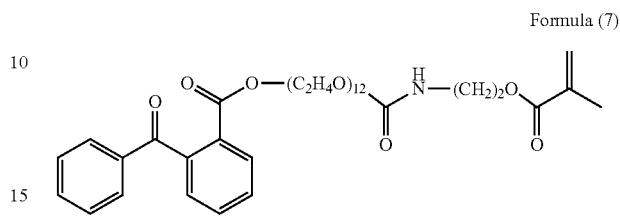

Example 8

To 15 mL of super dehydrated methylene chloride (manufactured by Wako Pure Chemical Industries, Ltd.), 3.53 g (25 mmol) of 2-isocyanatoethyl methacrylate (Karenz MOI, manufactured by SHOWA DENKO K.K.), 10.07 g (25 mmol) of intermediate 5, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 8.40 g of active-energy-ray-polymerizable initiator (JK-8) according to an embodiment of the present invention having a structure represented by formula (8).

Formula (8)

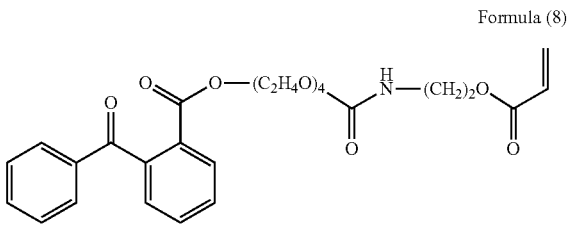

Example 9

To 15 mL of super dehydrated methylene chloride (manufactured by Wako Pure Chemical Industries, Ltd.), 4.98 g (25 mmol) of 2-(2-isocyanatoethoxy) ethylmethacrylate (Karenz MOI-EG, manufactured by SHOWA DENKO K.K.), 6.76 g (25 mmol) of 2-benzoyl-(2-hydroxyethyl benzoate) (intermediate 1), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 13.50 g of active-energy-ray-polymerizable initiator (JK-9) according to an embodiment of the present invention having a structure represented by formula (9).

Formula (9)

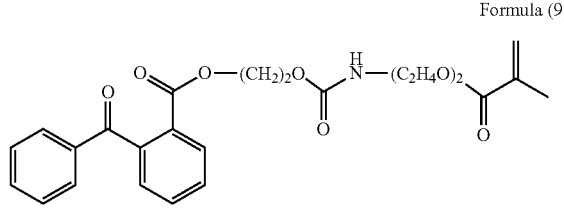

Example 10

To 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 8.16 g (25 mmol) of 2-benzoyl-(6-hydroxyhexyl benzoate) (intermediate 2), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 8.10 g of active-energy-ray-polymerizable initiator (JK-10) according to an embodiment of the present invention having a structure represented by formula (10).

Formula (10)

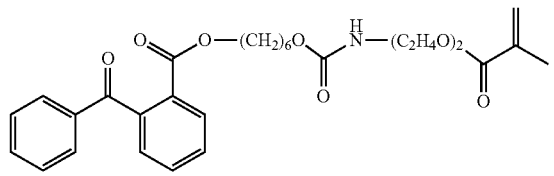

Example 11

To 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 11.67 g (25 mmol) of 2-benzoyl-(6-hydroxyhexadecane benzoate) (intermediate 3), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 9.20 g of active-energy-ray-polymerizable initiator (JK-11) according to an embodiment of the present invention having a structure represented by formula (11).

Formula (11)

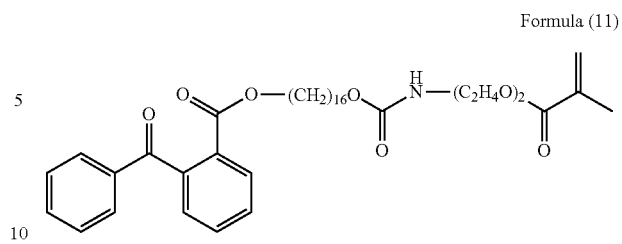

Example 12

To 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWADENKO K.K.), 7.86 g (25 mmol) of intermediate 4, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 7.70 g of active-energy-ray-polymerizable initiator (JK-12) according to an embodiment of the present invention having a structure represented by formula (12).

Formula (12)

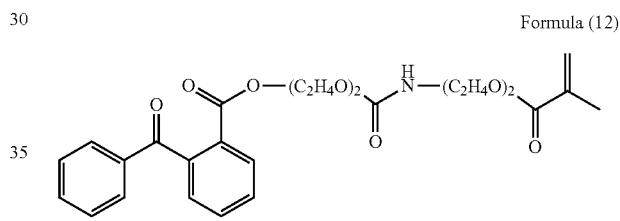

Example 13

To 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 10.06 g (25 mmol) of intermediate 5, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 9.50 g of active-energy-ray-polymerizable initiator (JK-13) according to an embodiment of the present invention having a structure represented by formula (13).

Formula (13)

Example 14

To 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 10.06 g (25 mmol) of intermediate 6, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 14.50 g of active-energy-ray-polymerizable initiator (JK-14) according to an embodiment of the present invention having a structure represented by formula (14).

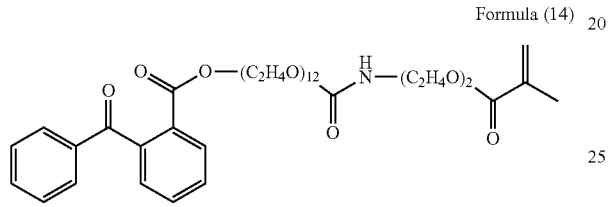

Formula (14)

Example 15

To 33.5 g (250 mmol) of dipropyleneglycol (manufactured by FUJIFILM Wako Pure Chemical Corporation), 0.49 g (5 mmol) of sulfuric acid (manufactured by KANTO CHEMICAL CO., INC.) was added, to which 11.31 g (50 mmol) of 2-benzoylbenzoic acid (Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 20.80 g of intermediate 7 having a structure represented by intermediate formula (7).

Intermediate 7

Subsequently, to 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 8.56 g (25 mmol) of intermediate 7, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 13.50 g of active-energy-ray-polymerizable initiator (JK-15) according to an embodiment of the present invention having a structure represented by formula (15).

Formula (15)

Example 16

To 48.1 g (250 mmol) of tripropyleneglycol (manufactured by Tokyo Chemical Industry Co., Ltd.), 0.49 g (5 mmol) of sulfuric acid (manufactured by KANTO CHEMICAL CO., INC.) was added, to which 11.31 g (50 mmol) of 2-benzoylbenzoic acid (Tokyo Chemical Industry Co., Ltd.) was added little by little while stirring, then heated to 120° C., and stirred for 4 hours. The mixture was cooled to room temperature, a resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 99/1) as an eluent to obtain 13.70 g of intermediate 8 having a structure represented by intermediate formula (8).

Intermediate 8

Subsequently, to 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 10.01 g (25 mmol) of intermediate 8, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 9.30 g of active-energy-ray-polymerizable initiator (JK-16) according to an embodiment of the present invention having a structure represented by formula (16).

Formula (16)

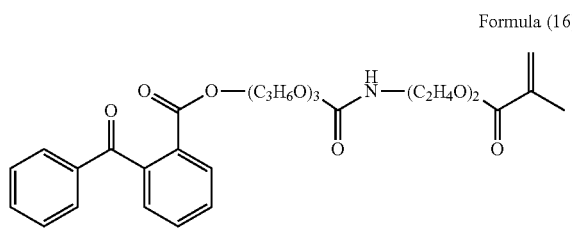

Example 17

To a mixture of 13.51 g (50 mmol) of 2-benzoyl-(2-hydroxyethyl benzoate) (intermediate 1) and 5.20 g (50 mmol) of 3-methoxypropanoic acid, 0.49 g (5 mmol) of sulfuric acid was added, which was heated to 120° C., and stirred for 4 hours. Then the mixture was cooled to room temperature, a resulting reaction solution was neutralized with a sodium hydrogencarbonate aqueous solution, to which 100 mL of ethyl acetate was added, and the mixture was washed with water. Subsequently, an organic phase was isolated, dried with magnesium sulfate to distill off the solvent. A residue was purified by silica gel column chromatography using a mixed solvent of ethyl acetate/methanol (volume ratio 98/2) as an eluent to obtain 12.20 g of intermediate 9a having a structure represented by intermediate formula (9a).

Intermediate Formula (9a)

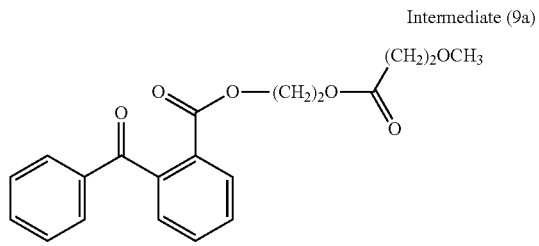

Subsequently, 8.90 g (25 mmol) of intermediate 9a was dissolved in 15 mL of super dehydrated methylene chloride (manufactured by Wako Pure Chemical Industries, Ltd.), and ice-cooled, to which a solution prepared by dissolving 20.0 g (80 mmol) of boron tribromide in 30 mL of super dehydrated methylene chloride (manufactured by Wako Pure Chemical Industries, Ltd.) was dripped. Then the ice cooling is terminated, and the mixture was stirred at room temperature for 24 hours, neutralized with 200 mL of ammonia aqueous solution. An organic phase was isolated, dried with magnesium sulfate to distill off the solvent. A residue was purified by silica gel column chromatography using a mixed solvent of ethyl acetate/methanol (volume ratio 98/2) as an eluent to obtain 6.70 g of intermediate 9b having a structure represented by intermediate formula (9b).

Intermediate Formula (9b)

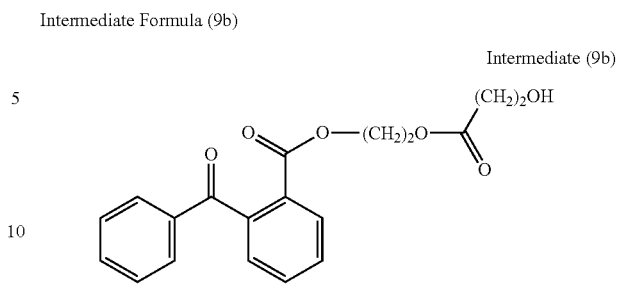

Subsequently, 6.85 g (20 mmol) of intermediate formula (9b) was dissolved in 10 mL of super dehydrated methylene chloride (manufactured by Wako Pure Chemical Industries, Ltd.), to which 2.43 g (24 mmol) of triethylamine was added. To the mixture, 1.81 g (20 mmol) of acrylic acid chloride was dripped, which was stirred at room temperature for 4 hours, and then the solvent was distilled off. A residue was purified by silica gel column chromatography using a mixed solvent of ethyl acetate/methanol (volume ratio 99/1) as an eluent to obtain 5.95 g of active-energy-ray-polymerizable initiator (JK-17) having a structure represented by formula (17).

Formula (17)

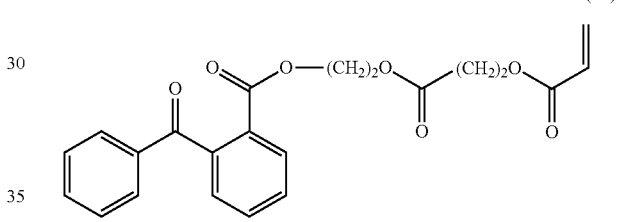

Example 18

To a mixture of 16.32 g (50 mmol) of 2-benzoyl-(2-hydroxyethyl benzoate) (intermediate 2) and 5.21 g (50 mmol) of 3-methoxypropanoic acid, 0.49 g (5 mmol) of sulfuric acid was added, which was heated to 120° C., and stirred for 4 hours. Then the mixture was cooled to room temperature. A resulting reaction solution was neutralized with a sodium hydrogencarbonate aqueous solution, to which 100 mL of ethyl acetate was added, and the mixture was washed with water. An organic phase was isolated, dried with magnesium sulfate to distill off the solvent. A residue was purified by silica gel column chromatography using a mixed solvent of ethyl acetate/methanol (volume ratio 98/2) as an eluent to obtain 11.80 g of intermediate 10a having a structure represented by intermediate formula (10a).

Intermediate Formula (10a)

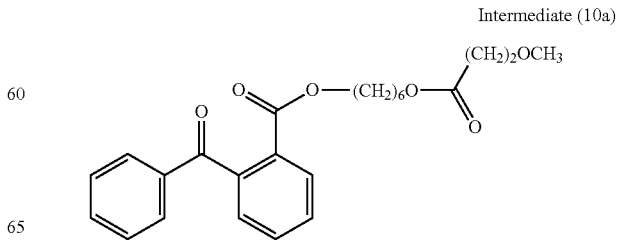

Subsequently, 9.98 g (25 mmol) of intermediate 10a was dissolved in 15 mL of super dehydrated methylene chloride (manufactured by Wako Pure Chemical Industries, Ltd.), and ice-cooled, to which a solution prepared by dissolving 20.1 g (80 mmol) of boron tribromide in 30 mL of super dehydrated methylene chloride (manufactured by Wako Pure Chemical Industries, Ltd.) under nitrogen gas stream was dripped. Then the ice cooling is terminated, and the mixture was stirred at room temperature for 24 hours, neutralized with 200 mL of ammonia aqueous solution. An organic phase was isolated, dried with magnesium sulfate to distill off the solvent. A residue was purified by silica gel column chromatography using a mixed solvent of ethyl acetate/methanol (volume ratio 98/2) as an eluent to obtain 7.60 g of intermediate 10b having a structure represented by intermediate formula (10b).

Intermediate Formula (10b)

Intermediate (10b)

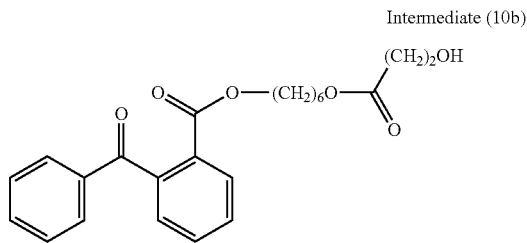

Subsequently, 7.97 g (20 mmol) of intermediate formula (10b) was dissolved in 10 mL of super dehydrated methylene chloride (manufactured by Wako Pure Chemical Industries, Ltd.), to which 2.40 g (24 mmol) of triethylamine was added. To the mixture, 1.81 g (20 mmol) of acrylic acid chloride was dripped under nitrogen gas stream, which was stirred at room temperature for 4 hours, and then the solvent was distilled off. A residue was purified by silica gel column chromatography using a mixed solvent of ethyl acetate/methanol (volume ratio 99/1) as an eluent to obtain 6.85 g of active-energy-ray-polymerizable initiator (JK-18) having a structure represented by formula (18).

Formula (18)

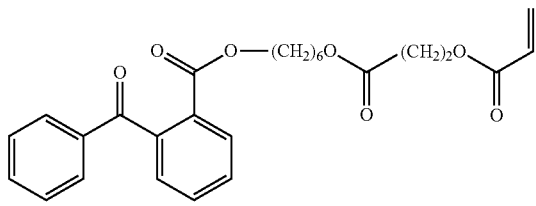

Example 19

To 50 mL of methylethylketone (manufactured by KANTO CHEMICAL CO., INC.), 9.92 g (50 mmol) of 2-hydroxybenzophenone (manufactured by FUJIFILM Wako Pure Chemical Corporation), 6.25 g (50 mmol) of 2-bromoethanol, and 9.68 g of potassium carbonate (manufactured by KANTO CHEMICAL CO., INC.) were added, which was refluxed for 24 hours. The mixture was cooled to room temperature, a resulting reaction solution was filtered through a glass filter, and the solvent was distilled off from the filtrate. A residue was purified by silica gel column chromatography using a mixed solvent of ethyl acetate/ hexane (volume ratio 2/8) as an eluent to obtain 9.88 g of 2-benzoyl-(2-hydroxyethoxy benzene) (intermediate 11).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 6.06 g (25 mmol) of 2-benzoyl-(2-hydroxyethoxy benzene) (intermediate 11), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 6.300 g of active-energy-ray-polymerizable initiator (JK-19) according to an embodiment of the present invention having a structure represented by formula (19).

Formula (19)

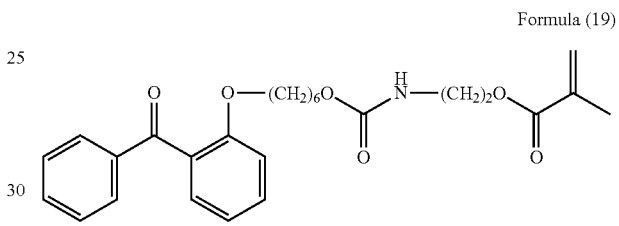

Example 20

To 60 mL of methylethylketone (manufactured by KANTO CHEMICAL CO., INC.), 9.92 g (50 mmol) of 2-hydroxybenzophenone (manufactured by FUJIFILM Wako Pure Chemical Corporation), 6.25 g (50 mmol) of 6-bromo-1-hexanol, and 9.68 g of potassium carbonate (manufactured by KANTO CHEMICAL CO., INC.) were added, which was refluxed for 24 hours. The mixture was cooled to room temperature, a resulting reaction solution was filtered through a glass filter, and the solvent was distilled off from the filtrate. A residue was purified by silica gel column chromatography using a mixed solvent of ethyl acetate/hexane (volume ratio 2/8) as an eluent to obtain 12.60 g of 2-benzoyl-(6-hydroxyhexanoxy benzene) (intermediate 12).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 7.46 g (25 mmol) of 2-benzoyl-(6-hydroxyhexanoxy benzene) (intermediate 12), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 6.25 g of active-energy-ray-polymerizable initiator (JK-20) according to an embodiment of the present invention having a structure represented by formula (20).

Formula (20)

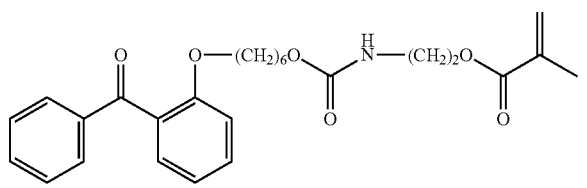

Example 21

To 80 mL of methylethylketone (manufactured by KANTO CHEMICAL CO., INC.), 9.92 g (50 mmol) of 2-hydroxybenzophenone (manufactured by FUJIFILM Wako Pure Chemical Corporation), 16.07 g (50 mmol) of 16-bromo-1-hexadecanol (manufactured by FUJIFILM Wako Pure Chemical Corporation), and 9.68 g of potassium carbonate (manufactured by KANTO CHEMICAL CO., INC.) were added, which was refluxed for 24 hours. The mixture was cooled to room temperature, a resulting reaction solution was filtered through a glass filter, and the solvent was distilled off from the filtrate. A residue was purified by silica gel column chromatography using a mixed solvent of ethyl acetate/hexane (volume ratio 2/8) as an eluent to obtain 15.65 g of 2-benzoyl-(16-hydroxyhexadecanoxy benzene) (intermediate 13).

Subsequently, to 15 mL of super dehydrated methylene chloride (manufactured by Wako Pure Chemical Industries, Ltd.), 3.88 g (25 mmol) of 2-isocyanatoethyl methacrylate (Karenz MOI, manufactured by SHOWA DENKO K.K.), 7.46 g (25 mmol) of 2-benzoyl-(16-hydroxyhexadecanoxy benzene) (intermediate 13), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 9.95 g of active-energy-ray-polymerizable initiator (JK-21) according to an embodiment of the present invention having a structure represented by formula (21).

Formula (21)

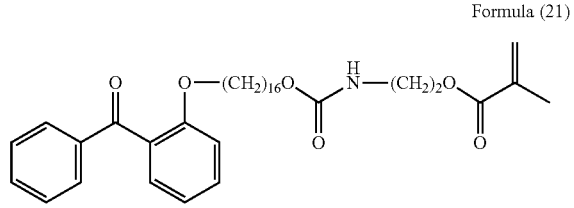

Example 22

Subsequently, to 15 mL of super dehydrated methylene chloride (manufactured by Wako Pure Chemical Industries, Ltd.), 3.53 g (25 mmol) of 2-isocyanatoethyl acrylate (Karenz AOI, manufactured by SHOWA DENKO K.K.), 7.46 g (25 mmol) of 2-benzoyl-(6-hydroxyhexanoxy benzene) (intermediate 12), and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 6.85 g of active-energy-ray-polymerizable initiator (JK-22) according to an embodiment of the present invention having a structure represented by formula (22).

Formula (22)

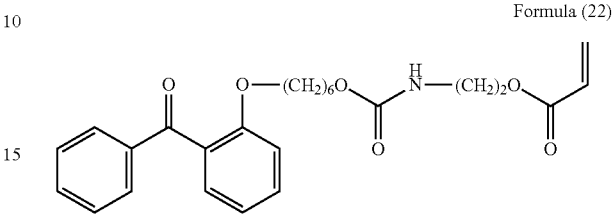

Example 23

To 60 mL of methylethylketone (manufactured by KANTO CHEMICAL CO., INC.), 9.92 g (50 mmol) of 2-hydroxybenzophenone (manufactured by FUJIFILM Wako Pure Chemical Corporation), 8.46 g (50 mmol) of 2-(2-bromoethoxy) ethanol (manufactured by FUJIFILM Wako Pure Chemical Corporation), and 9.68 g of potassium carbonate (manufactured by KANTO CHEMICAL CO., INC.) were added, which was refluxed for 24 hours. The mixture was cooled to room temperature, a resulting reaction solution was filtered through a glass filter, and the solvent was distilled off from the filtrate. A residue was purified by silica gel column chromatography using a mixed solvent of ethyl acetate/hexane (volume ratio 2/8) as an eluent to obtain 9.25 g of intermediate 14 having a structure represented by intermediate formula (14).

Intermediate Formula (14)

Intermediate 14

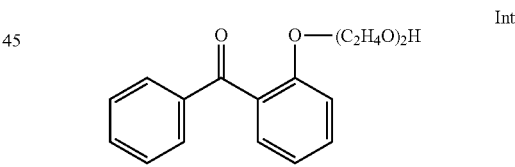

Subsequently, to 15 mL of super dehydrated methylene chloride (manufactured by Wako Pure Chemical Industries, Ltd.), 4.988 g (25 mmol) of 2-(2-isocyanatoethoxy)ethyl methacrylate (Karenz MOI-EG, manufactured by SHOWA DENKO K.K.), 7.16 g (25 mmol) of intermediate 14, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 7.25 g of active-energy-ray-polymerizable initiator (JK-23) according to an embodiment of the present invention having a structure represented by formula (23).

(Formula 23)

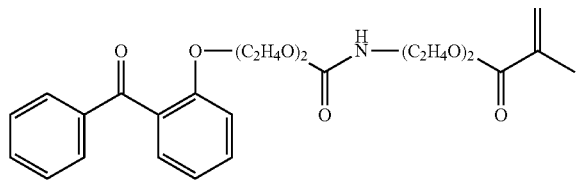

Formula (24)

Example 24

To 80 mL of methylethylketone (manufactured by KANTO CHEMICAL CO., INC.), 9.92 g (50 mmol) of 2-hydroxybenzophenone (manufactured by FUJIFILM Wako Pure Chemical Corporation), 12.87 g (50 mmol) of 2-(2-(2-(2-bromoethoxy)ethoxy)ethoxy)ethanol (manufactured by FUJIFILM Wako Pure Chemical Corporation), and 9.68 g of potassium carbonate (manufactured by KANTO CHEMICAL CO., INC.) were added, which was refluxed for 24 hours. The mixture was cooled to room temperature, a resulting reaction solution was filtered through a glass filter, and the solvent was distilled off from the filtrate. A residue was purified by silica gel column chromatography using a mixed solvent of ethyl acetate/hexane (volume ratio 2/8) as an eluent to obtain 12.30 g of intermediate 15 having a structure represented by intermediate formula (15).

Intermediate 15

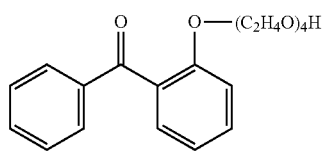

Subsequently, to 15 mL of super dehydrated methylene chloride (manufactured by Wako Pure Chemical Industries, Ltd.), 4.98 g (25 mmol) of 2-(2-isocyanatoethoxy)ethyl methacrylate (Karenz MOI-EG, manufactured by SHOWA DENKO K.K.), 7.16 g (25 mmol) of intermediate 15, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 8.20 g of active-energy-ray-polymerizable initiator (JK-24) according to an embodiment of the present invention having a structure represented by formula (24).

Example 25

To 15 mL of super dehydrated methylene chloride (manufactured by Wako Pure Chemical Industries, Ltd.), 3.53 g (25 mmol) of 2-isocyanatoethyl acrylate (Karenz AOI, manufactured by SHOWA DENKO K.K.), 9.37 g (25 mmol) of intermediate 15, and 0.009 g (0.015 mmol) of dibutyltin laurate (manufactured by Tokyo Chemical Industry Co., Ltd.) were added under nitrogen gas stream, which was stirred at room temperature for 4 hours. A resulting reaction solution was purified by silica gel column chromatography using a mixed solvent of ethyl acetate/methanol (volume ratio 99/1) as an eluent to obtain 8.90 g of active-energy-ray-polymerizable initiator (JK-25) according to an embodiment of the present invention having a structure represented by formula (25).

Formula (25)

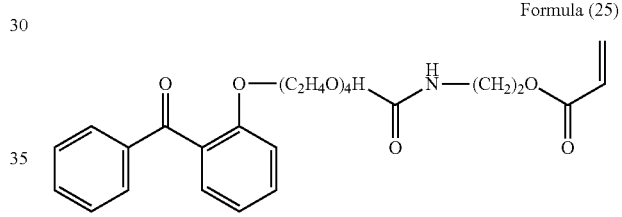

<<Evaluation of Active-Energy-Ray-Polymerizable Initiator>>

<Evaluation of Photoinitiator Function and Polymerizable Function>

Using a high-sensitivity differential scanning calorimeter (DSC7020, manufactured by SII NanoTechnology Inc.) equipped with a UV irradiator (LA-410UV, lamp: He-Xe Lamp MX4020, manufactured by HAYASHI-REPTC CO., LTD.), 10 mg of each active-energy-ray-polymerizable initiator prepared in Examples 1 to 25 was weighed out and put onto an aluminum pan, and irradiated with ultraviolet ray of 10 mW/cm² (wavelength standard: 365 nm) at room temperature for a certain time. The maximum calorific value (Hmax [mW]) and a time for reaching the maximum calorific value (Tmax [sec]) were measured to evaluate functions of the active-energy-ray-polymerizable initiator. The results are summarized in Table 1.

TABLE 1

| Example | Type | \multicolumn{5}{c}{Active-energy-ray-polymerizable initiator} | $H_{max}$ [mW] | $T_{max}$ [sec] |
|---|---|---|---|---|---|---|---|---|
| | | L1 | L2 | L3 | L4 | R | | |
| 1 | JK-1 | —COO— | —(CH$_2$)$_2$— | —NH— | —OC$_2$H$_4$— | —CH$_3$ | 7.8 | 8.5 |
| 2 | JK-2 | " | —(CH$_2$)$_2$— | " | " | " | 7.5 | 9.5 |
| 3 | JK-3 | " | —(CH$_2$)$_2$— | " | " | " | 7.4 | 10.2 |
| 4 | JK-4 | " | —(CH$_2$)$_2$— | " | " | —H | 7.5 | 9.5 |
| 5 | JK-5 | —COO— | —(OC$_2$H$_4$)$_2$— | —NH— | —OC$_2$H$_4$— | —CH$_3$ | 7.9 | 8.0 |
| 6 | JK-6 | " | —(OC$_2$H$_4$)$_4$— | " | " | " | 7.5 | 9.2 |
| 7 | JK-7 | " | —(OC$_2$H$_4$)$_{12}$— | " | " | " | 7.4 | 10.0 |

TABLE 1-continued

| Example | Active-energy-ray-polymerizable initiator | | | | | $H_{max}$ [mW] | $T_{max}$ [sec] |
|---|---|---|---|---|---|---|---|
| | Type | L1 | L2 | L3 | L4 | R | | |
| 8 | JK-8 | " | —(OC$_2$H$_4$)$_4$— | " | " | —H | 7.4 | 9.5 |
| 9 | JK-9 | —COO— | —(CH$_2$)$_2$— | —NH— | —(OC$_2$H$_4$)$_2$— | —CH$_3$ | 7.7 | 8.2 |
| 10 | JK-10 | " | —(CH$_2$)$_6$— | " | " | " | 7.1 | 9.1 |
| 11 | JK-11 | " | —(CH$_2$)$_{16}$— | " | " | " | 7.2 | 9.5 |
| 12 | JK-12 | —COO— | —(OC$_2$H$_4$)$_2$— | —NH— | —(OC$_2$H$_4$)$_2$— | —CH$_3$ | 7.4 | 8.8 |
| 13 | JK-13 | " | —(OC$_2$H$_4$)$_4$— | " | " | " | 7.7 | 9.4 |
| 14 | JK-14 | " | —(OC$_2$H$_4$)$_{12}$— | " | " | " | 7.3 | 10.0 |
| 15 | JK-15 | —COO— | —OC$_3$H$_6$— | —NH— | —(OC$_2$H$_4$)$_2$— | —CH$_3$ | 7.1 | 8.5 |
| 16 | JK-16 | " | —(OC$_3$H$_6$)$_3$— | " | " | " | 7.1 | 9.7 |
| 17 | JK-17 | —COO— | —(CH$_2$)$_2$— | — | —OC$_2$H$_4$— | —H | 7.1 | 8.2 |
| 18 | JK-18 | " | —(CH$_2$)$_6$— | " | " | " | 7.8 | 8.8 |
| 19 | JK-19 | —O— | —(CH$_2$)$_2$— | —NH— | —OC$_2$H$_4$— | —CH$_3$ | 7.7 | 8.5 |
| 20 | JK-20 | " | —(CH$_2$)$_6$— | " | " | " | 7.3 | 9.1 |
| 21 | JK-21 | " | —(CH$_2$)$_{16}$— | " | " | " | 7.2 | 9.5 |
| 22 | JK-22 | " | —(CH$_2$)$_6$— | " | " | —H | 7.0 | 9.4 |
| 23 | JK-23 | —O— | —(OC$_2$H$_4$)$_2$— | —NH— | —(OC$_2$H$_4$)$_2$— | —CH$_3$ | 7.5 | 8.8 |
| 24 | JK-24 | " | —(OC$_2$H$_4$)$_4$— | " | " | " | 7.6 | 9.4 |
| 25 | JK-25 | " | " | " | —OC$_2$H$_4$— | —H | 7.5 | 9.4 |

<<Preparation of Active-Energy-Ray-Polymerizable Composition>>

Examples 101 to 125

Each of active-energy-ray-polymerizable initiators prepared in Examples 1 to 25, 2-(2-vinyloxyethoxy)ethyl acrylate (manufactured by NIPPON SHOKUBAI CO., LTD.), dipentaerythritol hexaacrylate (A-DPH, manufactured by Shin-Nakamura Chemical Co., Ltd.)), dimethylaminopropylacrylamide, and 4-acryloylmorpholine were mixed in the constitution presented in Table 2 to obtain each of active-energy-ray-polymerizable compositions JK-1S to JK-25S according to embodiments of the present invention.

In Table 2, VEA represents 2-(2-vinyloxyethoxy)ethyl acrylate, DPH represents dipentaerythritol hexaacrylate, APA represents dimethylaminopropylacrylamide, and AMP represents 4-acryloylmorpholine.

<<Preparation of Active-Energy-Ray-Polymerizable Ink>>

Examples 201 to 203

A pigment dispersion GB-1 as a colorant including 16 parts by mass of carbon black (NIPEX 1504Q, manufactured by Orion Engineered Carbons SA), 6 parts by mass of pigment dispersant (Solsperse 32000, manufactured by Lubrizol Japan Limited), and 78 parts by mass of 2-phenoxyethyl acrylate (manufactured by Tokyo Chemical Industry Co., Ltd.); the active-energy-ray-polymerizable initiator prepared in Example 2, 10, or 20; 2-(2-vinyloxyethoxy)ethyl acrylate (manufactured by NIPPON SHOKUBAI CO., LTD.); and dipentaerythritol hexaacrylate (A-DPH, manufactured by Shin-Nakamura Chemical Co., Ltd.) were mixed in the constitution presented in Table 2 to obtain active-energy-ray-polymerizable inks JK-1Ink, JK-2Ink, and JK-3Ink according to embodiments of the present invention.

Examples 204 and 205

A pigment dispersion GB-2 as a colorant including 16 parts by mass of carbon black (NIPEX 150-IQ, manufactured by Orion Engineered Carbons SA), 4 parts by mass of pigment dispersant (BYKJET 9152, manufactured by BYK Additives & Instruments GmbH), and 80 parts by mass of ion-exchanged water; the active-energy-ray-polymerizable initiator prepared in Example 6 or 13; dimethylaminopropylacrylamide; and 4-acryloylmorpholine were mixed in the constitution presented in Table 2 to obtain the active-energy-ray-polymerizable inks JK-4Ink and JK-5Ink according to embodiments of the present invention.

<<Preparation of Comparative Active-Energy-Ray-Polymerizable Composition>>

Comparative Example 1

<Preparation of Pre-Preparation Product>

In accordance with Synthesis Example described in JP-5568092-B (corresponding to WO2010/069758 A1 and US2011/0224324A1, the disclosure of which is incorporated herein by reference), 7.5 g of Irgacure 127 (Ciba Specialty Chemicals Inc.) was dissolved in 31.4 g of 2-(2-vinyloxyethoxy)ethyl acrylate (manufactured by NIPPON SHOKUBAI CO., LTD.), to which 1 mol % of 2,6-di-t-butyl-4-methylphenol (manufactured by Tokyo Chemical Industry Co., Ltd.) was added based on 2-(2-vinyloxyethoxy)ethyl acrylate, and 5 mmol of trifluoroacetic acid was added based on Irgacure 127, and reacted at 50° C. for 4 hours. To the mixture, 25 g of pre-treated ion exchange resin was added, and the reaction mixture was stirred for 1 hour, from which the ion exchange resin was removed by filtration to obtain a pre-preparation product Y1 containing a comparative active-energy-ray-polymerizable initiator RJK-1 having a structure represented by formula (26).

Formula (26)

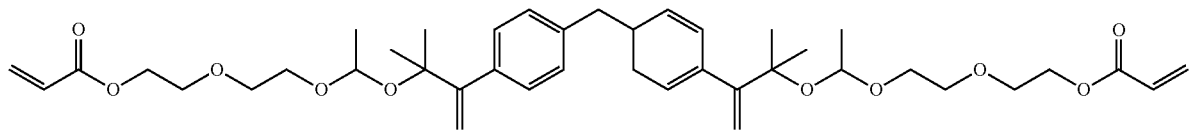

<Preparation of Comparative Active-Energy-Ray-Polymerizable Composition>

The pre-preparation product Y1 prepared above, 2-(2-vinyloxyethoxy)ethyl acrylate (manufactured by NIPPON SHOKUBAI CO., LTD.), dipentaerythritol hexaacrylate (A-DPH, manufactured by Shin-Nakamura Chemical Co., Ltd.) were mixed in the constitution presented in Table 2 to obtain a comparative active-energy-ray-polymerizable composition RJK-1S.

Comparative Example 2

<Preparation of Pre-Preparation Product>

In the same manner as in the above Comparative Example 1, 2.5 g of 9-oxo-9H-thioxanthene-2-carboxylic acid-3-(4-acryloyloxy-butoxy) 2-hydroxy-propyl ester obtained in accordance with Synthesis Example described in JP-5568092-B (corresponding to WO2010/069758 A1 and US2011/0224324A1, the disclosure of which is incorporated herein by reference) was dissolved in 10.5 g of 2-(2-vinyloxyethoxy)ethyl acrylate (manufactured by NIPPON SHOKUBAI CO., LTD.), to which 1 mol % of 2,6-di-t-butyl-4-methylphenol (manufactured by Tokyo Chemical Industry Co., Ltd.) was added based on 2-(2-vinyloxyethoxy)ethyl acrylate, and 5 mmol of trifluoroacetic acid was added based on 9-oxo-9H-thioxanthene-2-carboxylic acid-3-(4-acryloyloxy-butoxy) 2-hydroxy-propyl ester, and reacted at 50° C. for 2 hours. To the mixture, 25 g of pre-treated ion exchange resin was added, and the reaction mixture was stirred for 1 hour, from which the ion exchange resin was removed by filtration to obtain a pre-preparation product Y2 containing a comparative active-energy-ray-polymerizable initiator RJK-2 having a structure represented by formula (27).

In Table 2, STIN-5 represents 4-(2-acryloyloxyethoxy)phenyl-2-hydroxy-2-propylketone, and COINI-1 represents 4-(dimethylamino)benzoic acid 2-(acryloyloxy)ethyl ester.

<<Preparation of Comparative Active-Energy-Ray-Polymerizable Ink>>

Comparative Examples 3 and 4

In the same manner as in Example 201, the comparative active-energy-ray-polymerizable initiator, the pigment dispersion GB-1, 2-(2-vinyloxyethoxy)ethyl acrylate (manufactured by NIPPON SHOKUBAI CO., LTD.), and dipentaerythritol hexaacrylate (A-DPH, manufactured by Shin-Nakamura Chemical Co., Ltd.) were mixed in the constitution presented in Table 2 to obtain comparative active-energy-ray-polymerizable inks RJK-1Ink and RJK-2Ink.

<<Polymerization Product Obtained from Active-Energy-Ray-Polymerizable Composition>>

The active-energy-ray-polymerizable composition in each of Examples and Comparative Examples was applied on a polyethylene terephthalate (PET) film (film thickness: 100 μm) while adjusting a wire bar so that an adhesion amount is 10 g/m². Immediately after that, the composition was irradiated with ultraviolet ray having an intensity of 20 mW/cm² at a wavelength reference of 365 nm using an ultrahigh pressure mercury lamp light source apparatus (SX-UI 501 HR, manufactured by USHIO INC.) equipped with a power supply (BA-H501R, manufactured by USHIO INC.) in air for 10 seconds to obtain a polymer on the PET film.

Formula (27)

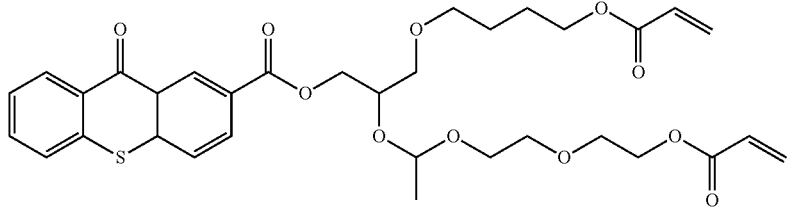

<Preparation of Comparative Active-Energy-Ray-Polymerizable Composition>

Subsequently, the pre-preparation product Y2 prepared above, 2-(2-vinyloxyethoxy)ethyl acrylate (manufactured by NIPPON SHOKUBAI CO., LTD.), dipentaerythritol hexaacrylate (A-DPH, manufactured by Shin-Nakamura Chemical Co., Ltd.), 4-(2-acryloyloxyethoxy) phenyl-2-hydroxy-2-propylketone, and 4-(dimethylamino)benzoic acid 2-(acryloyloxy)ethyl ester were mixed in the constitution presented in Table 2 to obtain a comparative active-energy-ray-polymerizable composition RJK-2S.

<<Polymer Obtained from Active-Energy-Ray-Polymerizable Ink>>

<Image Forming Process>

Using an inkjet recording apparatus (IPSiO GXe-5500, manufactured by Ricoh Co., Ltd.) and the active-energy-ray-polymerizable ink in each of Examples and Comparative Examples, a solid image of 5 cm×20 cm was printed on a PET film (film thickness: 100 μm) in a manner that a drive voltage of a piezoelement was adjusted so that an ink adhesion amount (adhesion amount after the subsequent drying at 100° C.) was 10 g/m² and a printing mode of the apparatus is set to "plain paper_clean", under an environmental condition adjusted to 23±0.5° C. and 50±5% RH.

<Preparation of Polymer>

Subsequently, the PET film on which the solid image had been printed was left in a drying oven heated to 100° C. for 30 seconds. Immediately after that, the composition was irradiated with ultraviolet ray having an intensity of 20 mW/cm² at the wavelength reference of 365 nm using the ultrahigh pressure mercury lamp light source apparatus (SX-UI 501 HR, manufactured by USHIO INC.) equipped with the power supply (BA-H501R, manufactured by USHIO INC.) in air for 10 seconds to obtain a polymer on the PET film.

mixed. The mixture was filtered through a 0.45 μm filter, then the sample was injected into a gas chromatography mass spectrometer (GC-MS) to quantify the leaving and moving components. The results are summarized in Table 2. Conditions of GC-MS are described below.

Apparatus of main body: GCMS2010 manufactured by SHIMADZU CORPORATION
Column: DB-5MS manufactured by Agilent Technologies, Inc.
Measurement condition: preservation at 50° C. for 0.5 minute, then heating at a rate of 20° C./min, and then preservation at 300° C. for 0.5 minute
Measurement mode: Selected Ion Monitoring (SIM)
Injection volume: 10 μL

TABLE 2

| Example | Active-energy-ray-polymerizable composition or ink | Active-energy-ray-polymerizable Initiator Type | [parts by mass] | VEA [parts by mass] | DPH [parts by mass] | APA [parts by mass] | AMP [parts by mass] | STIN-5 [parts by mass] | COIN-1 [parts by mass] | Colorant Type | [parts by mass] | Eluted quantity [mg/m²] |
|---|---|---|---|---|---|---|---|---|---|---|---|---|
| 101 | JK-1S | JK-1 | 50.0 | 29.0 | 20.0 | — | — | — | — | — | — | 0.4 |
| 102 | JK-2S | JK-2 | 50.0 | 29.0 | 20.0 | — | — | — | — | — | — | 0.4 |
| 103 | JK-3S | JK-3 | 50.0 | 29.0 | 20.0 | — | — | — | — | — | — | 0.4 |
| 104 | JK-4S | JK-4 | 50.0 | 29.0 | 20.0 | — | — | — | — | — | — | 0.4 |
| 105 | JK-5S | JK-5 | 50.0 | — | — | 29.0 | 20.0 | — | — | — | — | 0.7 |
| 106 | JK-6S | JK-6 | 50.0 | — | — | 29.0 | 20.0 | — | — | — | — | 0.7 |
| 107 | JK-7S | JK-7 | 50.0 | — | — | 29.0 | 20.0 | — | — | — | — | 0.8 |
| 108 | JK-8S | JK-8 | 50.0 | — | — | 29.0 | 20.0 | — | — | — | — | 0.7 |
| 109 | JK-9S | JK-9 | 50.0 | 29.0 | 20.0 | — | — | — | — | — | — | 0.4 |
| 110 | JK-10S | JK-10 | 50.0 | 29.0 | 20.0 | — | — | — | — | — | — | 0.4 |
| 111 | JK-11S | JK-11 | 50.0 | 29.0 | 20.0 | — | — | — | — | — | — | 0.5 |
| 112 | JK-12S | JK-12 | 50.0 | — | — | — | 20.0 | — | — | — | — | 0.7 |
| 113 | JK-13S | JK-13 | 50.0 | — | — | — | 20.0 | — | — | — | — | 0.7 |
| 114 | JK-14S | JK-14 | 50.0 | — | — | — | 20.0 | — | — | — | — | 0.9 |
| 115 | JK-15S | JK-15 | 50.0 | 29.0 | 20.0 | — | — | — | — | — | — | 0.4 |
| 116 | JK-16S | JK-16 | 50.0 | 29.0 | 20.0 | — | — | — | — | — | — | 0.4 |
| 117 | JK-17S | JK-17 | 50.0 | 29.0 | 20.0 | — | — | — | — | — | — | 0.4 |
| 118 | JK-18S | JK-18 | 50.0 | 29.0 | 20.0 | — | — | — | — | — | — | 0.5 |
| 119 | JK-19S | JK-19 | 30.0 | 9.0 | 20.0 | — | — | 20.0 | 20.0 | — | — | 0.2 |
| 120 | JK-20S | JK-20 | 30.0 | 9.0 | 20.0 | — | — | 20.0 | 20.0 | — | — | 0.2 |
| 121 | JK-21S | JK-21 | 30.0 | 9.0 | 20.0 | — | — | 20.0 | 20.0 | — | — | 0.3 |
| 122 | JK-22S | JK-22 | 30.0 | 9.0 | 20.0 | — | — | 20.0 | 20.0 | — | — | 0.3 |
| 123 | JK-23S | JK-23 | 30.0 | 9.0 | 20.0 | — | — | 20.0 | 20.0 | — | — | 0.2 |
| 124 | JK-24S | JK-24 | 30.0 | 9.0 | 20.0 | — | — | 20.0 | 20.0 | — | — | 0.2 |
| 125 | JK-25S | JK-25 | 30.0 | 9.0 | 20.0 | — | — | 20.0 | 20.0 | — | — | 0.2 |
| 201 | JK-1Ink | JK-2 | 35.0 | 17.0 | 10.0 | — | — | — | — | GB-1 | 37.0 | 0.9 |
| 202 | JK-2Ink | JK-10 | 35.0 | 17.0 | 10.0 | — | — | — | — | GB-1 | 37.0 | 0.8 |
| 203 | JK-3Ink | JK-20 | 30.0 | 2.0 | 10.0 | — | — | 10.0 | 10.0 | GB-1 | 37.0 | 0.8 |
| 204 | JK-4Ink | JK-6 | 35.0 | — | — | 17.0 | 10.0 | — | — | GB-2 | 37.0 | 0.9 |
| 205 | JK-5Ink | JK-13 | 30.0 | — | — | 20.0 | 12.0 | — | — | GB-2 | 37.0 | 0.9 |
| Comparative Example 1 | RJK-1S | RJK-1 | 50.0 | 29.0 | 20.0 | — | — | — | — | — | — | 2.5 |
| Comparative Example 2 | RJK-2S | RJK-2 | 30.0 | 9.0 | 20.0 | — | — | 20.0 | 20.0 | — | — | 2.2 |
| Comparative Example 3 | RJK-1Ink | RJK-1 | 35.0 | 17.0 | 10.0 | — | — | — | — | GB-1 | 37.0 | 12.5 |
| Comparative Example 4 | RJK-2Ink | RJK-2 | 30.0 | 2.0 | 10.0 | — | — | 10.0 | 10.0 | GB-1 | 37.0 | 17.5 |

<<Evaluation for Amount of Components Leaving and Moving from Polymer>>

A sample was cut out from each polymer (adhesion amount: 10 g/cm²) on the PET, obtained from each active-energy-ray-polymerizable composition and ink, and each comparative active-energy-ray-polymerizable composition and ink so that an area of the sample was 7.068×2 cm². The cut sample was added to a 50 mL beaker containing 4.5 mL of acetonitrile, and extracted by ultrasonication for 30 minutes. About 4.5 mL of extract was transferred to a 5 mL volumetric flask, and the sample was rinsed twice with 5 mL of acetonitrile in a total volume of 5 mL together with the extract, and the extract and the rinse liquid were thoroughly From the results in Tables 1 and 2, it was found that the polymerizable composition and ink using the active-energy-ray-polymerizable initiator according to an embodiment of the present invention exhibit an excellent polymerization speed in response to the active-energy-ray, and are sufficiently prevented from leaving from a polymerization product or moving to a contact object.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. An active-energy-ray-polymerizable initiator having a structure represented by the following general formula (1):

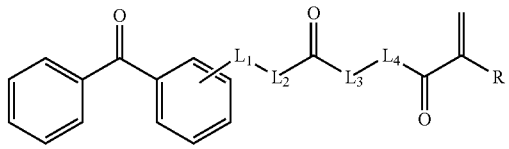

General Formula (1)

wherein:
- $L_1$ represents —C(=O)—O— (binding to $L_2$ side) or —O—,
- $L_2$ represents —O(CH$_2$)$_p$-(binding to $L_1$ side), —(OC$_2$H$_4$)$_n$-(binding to $L_1$ side), or —(OC$_3$H$_6$)$_m$-(binding to $L_1$ side), where p represents an integer of 2 to 16, n represents an integer of 2 to 12, and m represents 2 or 3,
- $L_3$ represents a direct binding or —NH—,
- $L_4$ represents —OC$_2$H$_4$-(binding to $L_3$ side) or —(OC$_2$H$_4$)$_2$-(binding to $L_3$ side), and
- R represents —H or —CH$_3$.

2. The active-energy-ray-polymerizable initiator according to claim 1, wherein $L_3$ represents —NH—.

3. The active-energy-ray-polymerizable initiator according to claim 1, wherein $L_2$ represents —(OC$_2$H$_4$)$_n$-(binding to $L_1$ side), and n represents an integer of 3 to 12.

4. An active-energy-ray-polymerizable composition comprising the active-energy-ray-polymerizable initiator according to claim 1.

5. An active-energy-ray-polymerizable ink comprising the active-energy-ray-polymerizable initiator according to claim 1.

6. A water-based active-energy-ray-polymerizable ink comprising the active-energy-ray-polymerizable initiator according to claim 3.

7. An ink storage container comprising:
a container; and
the ink according to claim 5 stored in the container.

8. An image forming method comprising:
discharging the ink according to claim 5 onto a recording medium to form an image.

9. An image forming apparatus comprising:
an ink storage container storing the ink according to claim 5; and
a discharging device configured to discharge the ink stored in the ink storage container onto a recording medium.

* * * * *